United States Patent [19]

Nichols

[11] 4,275,731

[45] Jun. 30, 1981

[54] SUCTION CANISTER WITH VORTEX FLOW DEFLECTOR

[76] Inventor: Robert L. Nichols, 800 Fort Worth St., Jacksonville, Tex. 75766

[21] Appl. No.: 923,391

[22] Filed: Jul. 10, 1978

[51] Int. Cl.³ .............................................. A61M 1/00
[52] U.S. Cl. .................................. 128/276; 137/205; 15/353
[58] Field of Search ................... 137/205, 592; 141/59, 141/286; 128/275, 276, 277, 278, DIG. 3; 15/353

[56] References Cited

U.S. PATENT DOCUMENTS

| | | | |
|---|---|---|---|
| 1,325,991 | 12/1919 | King | 141/286 |
| 2,791,355 | 5/1957 | Morgan, Jr. | 141/286 |
| 3,597,902 | 8/1971 | Williams | 15/353 |
| 3,605,786 | 9/1971 | Machin | 137/205 |
| 3,618,297 | 11/1971 | Hamrick | 15/353 |
| 3,646,935 | 3/1972 | Holbrook | 128/276 |
| 3,648,698 | 3/1972 | Doherty | 128/276 |
| 3,685,517 | 8/1972 | Reynolds et al. | 128/277 |
| 3,699,815 | 10/1972 | Holbrook | 73/427 |
| 3,719,197 | 3/1973 | Pannier et al. | 137/205 |
| 3,805,788 | 4/1974 | Kleiner | 128/276 |
| 3,881,640 | 5/1975 | Noble | 128/214 C |
| 3,965,902 | 6/1976 | Reilly et al. | 128/276 |
| 3,965,903 | 6/1976 | Cranage | 128/276 |
| 3,989,046 | 11/1976 | Pannier et al. | 128/276 |
| 4,013,076 | 3/1977 | Puderbaugh et al. | 128/276 |
| 4,047,526 | 9/1977 | Reynolds et al. | 128/276 |
| 4,111,225 | 9/1978 | Phelps | 137/592 |

FOREIGN PATENT DOCUMENTS 2314791 10/1974 Fed. Rep. of Germany ............ 15/353
384391 2/1965 Switzerland ............................. 141/286

OTHER PUBLICATIONS

Webster's Seventh New Collegiate Dictionary, G & C Merriam Co., Springfield, Mass., 1963, p. 439 "integral".

Primary Examiner—Robert W. Michell
Assistant Examiner—J. L. Kruter

[57] ABSTRACT

The specification discloses a suction system for draining fluid from a source. The system includes a canister and a cover having suction and fluid receiving ports. The fluid port includes a fluid receiving tube disposed below the canister cover. The fluid receiving tube receives fluid from the source and directs the fluid downwardly into the canister. A deflecting surface is provided on the lower portion of the fluid receiving tube for deflecting the received fluid to tangentially impinge the interior walls of the canister. The received fluid is directed by the deflecting surface to flow in a substantially helical path around the interior walls of the canister to retard the flow of the received fluid within the canister to effectively prevent aerosol droplet generation and subsequent entry of the aerosol droplets into the suction port of the canister.

1 Claim, 3 Drawing Figures

SUCTION CANISTER WITH VORTEX FLOW DEFLECTOR

FIELD OF THE INVENTION

This invention relates to medical suction canister assemblies for effectively draining fluid from a patient, and more particularly to a vortex flow deflector for deflecting fluid flowing into suction canisters.

THE PRIOR ART

During the course of a surgical operation on a patient, it is often necessary to remove from the site of the operation various body fluids including blood, clots and other viscid fluids which tend to collect at the operation site. Removal of such body fluids is generally accomplished using an aspirator connected to a source of vacuum to draw the fluids through a suitable tube for deposit into a collection bottle or canister.

Body fluid storage canisters for use in such systems are well known in the art. Typically, such canister assemblies include a canister and cover which are secured together with a leak tight seal. Two connections are provided in the cover, a vacuum port for being connected by a tube or other suitable connections to a source of vacuum, for example, a vacuum pump or hospital vacuum outlet station. The other connection comprises a fluid receiving port which is connected through a drainage tube to the surgical operating site on a patient.

In the suction canister, a vacuum is produced to create a vacuum in the tube leading to the operation site from which fluids are to be withdrawn. This vacuum carries the fluid through the drainage tube to an inlet in the suction canister. Since the fluid enters the suction canister at high velocities, its contact with the sidewalls and bottom of the suction canister causes the fluid to splash within the suction canister. The high velocity impact of the fluid against the canister sidewalls, the bottom wall of the suction canister and the fluid interface causes the molecular attraction of the fluid to weaken such that aerosol droplets or particles are generated within the suction canister.

Moreover, the impact of the fluid stream from the fluid receiving port against the fluid interface often causes a fluid swell or wave which causes the fluid to move and splash adjacent the vacuum port. The presence of aerosol droplets, fluids splashing and waves within the suction canister can cause fluid particles to enter the vacuum port of the suction canister. In prior collection canisters, these aerosol particles can be entrained in the air being drawn out of the vacuum port and therefore be deposited in the vacuum tubing, regulators and the vacuum source. Such aerosol particles are not only dangerous because they can carry bacteria and the like, but the particles can also cause corrosion and other damage to the vacuum regulators and to the vacuum system itself. Further, continuous deposits of such aerosol particles can tend to build up on the interior of the vacuum system tubing and reduce the effective interior aperture of the tubing. It is therefore highly undesirable that aerosol droplets be generated and entrained in the air within suction canisters.

The prior art has provided various devices for carrying fluid to the bottom of suction canisters and for directing fluid to the sidewalls of suction canisters in order to tend to reduce splashing and generation of aerosol droplets. Such prior art devices which deflect inlet fluid toward the sidewall of suction canisters include those described and claimed in U.S. Pat. No. 3,989,046, issued to Pannier, Jr. et al. on Nov. 2, 1976 and entitled "Asceptic Disposable Rigid Receiver for Body Drainage;" U.S. Pat. No. 3,965,902, issued to Reilly et al. on June 29, 1976 and entitled "Disposable Fluid Collection Container;" and U.S. Pat. No. 3,805,788, issued to Kleiner on Apr. 23, 1974 and entitled "Aspirator Jar." Additionally, several prior art devices have attempted to reduce or prevent splashing and aerosol droplet generation by directing inlet fluid downwardly towards the bottom of the suction canister or below the level of fluid collected within the suction canister. These prior art devices include those described and claimed in U.S. Pat. No. 3,965,903, issued to Cranage on June 29, 1976 and entitled "Suction Bottle Assembly;" U.S. Pat. No. 3,719,197 issued to Pannier Jr. et al. on Mar. 6, 1973 and entitled "Asceptic Suction Drainage System and Valve Therefor;" U.S. Pat. No. 3,648,698, issued to Doherty on Mar. 14, 1972 and entitled "Surgical Collection Unit;" U.S. Pat. No. 3,646,935, issued to Holbrook et al. on Mar. 7, 1972 and entitled "Fluid Collection Systems;" and U.S. Pat. No. 3,605,786, issued to Machin, Jr. on Sept. 20, 1961 and entitled "Evacuator."

Such prior art devices have not been completely successful in minimizing nor effectively controlling splashing, bounce and aerosol droplet generation of fluids entering vacuum canisters during the course of a surgical operation. Inlet fluid directed to directly impact the sidewalls of suction canisters, due to the high impact fluid velocity, causes the inlet fluid molecular attraction to decrease and thereby causing the generation of aerosol droplets. Fluid which is deflected downwardly causes increased splashing and aspiration of fluid directly into the vacuum port of the suction canister. Fluid entering below the level of fluid in the suction canister can also create a large wave within the suction canister.

A need has thus arisen for a fluid deflector for use in a suction canister for effecting drainage from a patient in which the deflector substantially eliminates aerosol droplet generation and entry of fluid into the vacuum port of suction canisters. A need has further arisen for a deflector which slows the velocity of inlet fluid such that the impact velocity of the inlet fluid against the sidewalls of suction canisters and collected fluid within suction canisters is such that the molecular attraction between the molecules of the inlet fluid is retained to thereby prevent generation of aerosol droplets.

SUMMARY OF THE INVENTION

In accordance with the present invention, a deflector is provided for use with a suction canister assembly for retarding the flow of received fluid within the suction canister to effectively prevent aerosol droplet generation and entry of fluid into the suction port of the suction canister.

In accordance with the present invention, in a suction system for draining fluid from a source, wherein the system includes a canister and a cover having suction and fluid receiving ports, a deflector is provided and includes a fluid receiving tube. The fluid receiving tube is disposed within the fluid receiving port and extends below the canister cover. The fluid receiving tube is adapted for receiving fluid from the source and for deflecting the received fluid to tangentially impinge against the interior walls of the canister. The received fluid is thereby directed to flow in a substantially helical path around the interior walls of the canister thereby retarding the flow of the received fluid within the canister to effectively prevent aerosol droplet generation and entry of fluid into the suction port.

In accordance with another aspect of the present invention, a suction system for receiving and retaining fluids drained from a source includes a canister having a closed bottom, substantially cylindrical sidewalls and an open mouth portion. A closure member is provided and is adapted to selectively close the open mouth portion of the canister. The closure member includes an inlet port for admitting fluid into the interior of the canister and an outlet port for withdrawing air from the interior of the canister. A deflector is disposed within the closure member inlet port and extends below the closure member. The deflector includes structure for deflecting fluid admitted into the canister through the inlet port tangentially against the cylindrical sidewalls. The admitted fluid is directed to flow in a substantially helical path around the cylindrical sidewalls to thereby retard the flow of admitted fluid within the canister to prevent the admitted fluid from impinging at high velocities against the bottom of the canister and collected fluid within the canister to thereby effectively prevent aerosol droplet generation and entry of admitted fluid into the outlet port.

DESCRIPTION OF THE DRAWINGS

For a more complete understanding of the present invention and for further objects and advantages thereof, reference is now made to the following detailed description taken in conjunction with the accompanying drawings, in which.

DESCRIPTION OF THE PREFERRED EMBODIMENT

Figure 1:
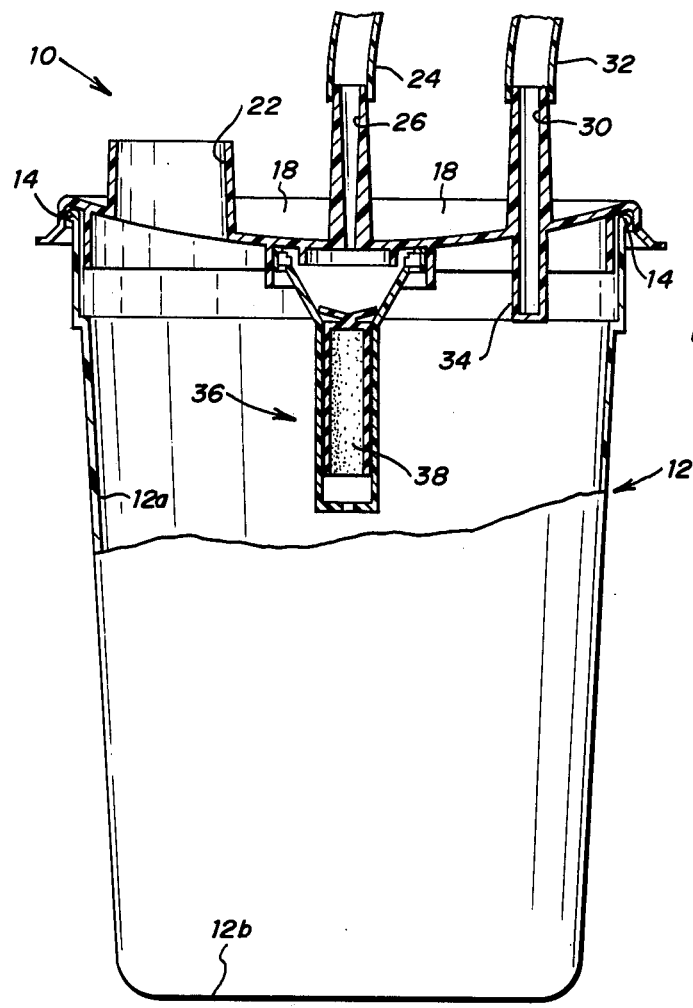
FIG. 1 is a side elevational view, partially in section, illustrating a suction canister utilizing the deflector of the present invention.

FIG. 1 illustrates a suction canister assembly generally identified by the numeral 10 utilizing the present invention. Suction canister assembly 10 includes a suction canister generally identified by the numeral 12, which may be formed of impact resistant, clear polystyrene to provide an implosion proof canister. Suction canister 12 has an elongated, slightly tapered configuration with a curved lip 14. Suction canister 12 is provided with a cover member 18 which is secured in a fluid tight relationship to curved lip 14 of suction canister 12 as is well known in the art.

Cover member 18 includes a pour spout 22 for ease in emptying collected fluid contained within suction canister 12. A source of vacuum, for example, a vacuum pump or hospital vacuum outlet stations, is applied through a tube 24 which is received by a vacuum port 26 integrally formed with cover member 18. Cover member 18 further includes a fluid inlet port 30 interconnected to a tube 32 which extends to a patient from which drainage is to be effected. Integrally formed with fluid inlet port 30 and cover member 18 is the deflector 34 of the present invention. Deflector 34 directs the fluid tangentially to the canister sidewall and substantially reduces the generation of aerosol droplets and particles. The construction of deflector 34 will be subsequently described in detail in connection with FIG. 2.

Associated with vacuum port 26 is a vacuum shut-off valve generally identified by the numeral 36. Vacuum shut-off valve 36 includes a float 38 which functions to seal against vacuum port 26 when a predetermined level of fluid is reached within suction canister 12 to shut-off the vacuum pressure applied to suction canister assembly 10.

In operation of suction canister assembly 10, vacuum pressure is applied through tube 24 to vacuum port 26 through shut-off valve assembly 36. This vacuum pressure carries fluid through tube 32 through suction port 30 and deflector 34 into suction canister 12. As suction canister 12 gradually fills, float 38 will rise, generally vertically, moving to close vacuum port 26 to prevent further fluid from being drained from the patient into suction canister 12.

Figure 2:
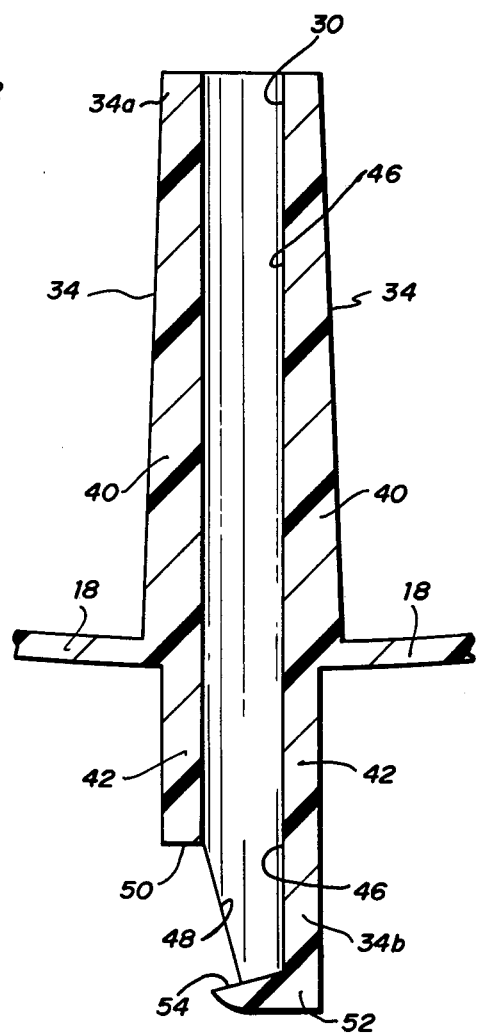
FIG. 2 is an enlarged side elevational view, in section, of the deflector of the present invention.

Referring to FIG. 2, deflector 34 is illustrated having an upper end 34a and a lower end 34b. Fluid inlet port 30 is disposed in the upper end 34a of deflector 34. Deflector 34 includes sidewalls 40 which are disposed above cover member 18. Sidewalls 40 are slightly tapered from the surface of cover member 18 toward upper end 34a to receive tube 32 (FIG. 1). Disposed below cover member 18 are sidewalls 42 of deflector 34. Sidewalls 40 and 42 define an interior bore 46 of substantially constant diameter extending the length of deflector 34. Disposed adjacent lower end 34b of deflector 34 is an aperture 48, more clearly illustrated in FIG. 3. Aperture 48 is disposed at an angle to the vertical axis of bore 46 and is defined by top and bottom walls 50 and 52. Bottom wall 52 partially closes bore 46 at lower end 34b of deflector 34 and includes an upper surface 54. Upper surface 54 of bottom wall 52 is downwardly inclined towards the bottom 12b (FIG. 1) of suction canister 12.

Although FIG. 2 illustrates deflector 34 as being integrally formed with cover member 18, in the alternative, deflector 34 may be independently fabricated for insertion into an aperture in cover member 18.

Figure 3:
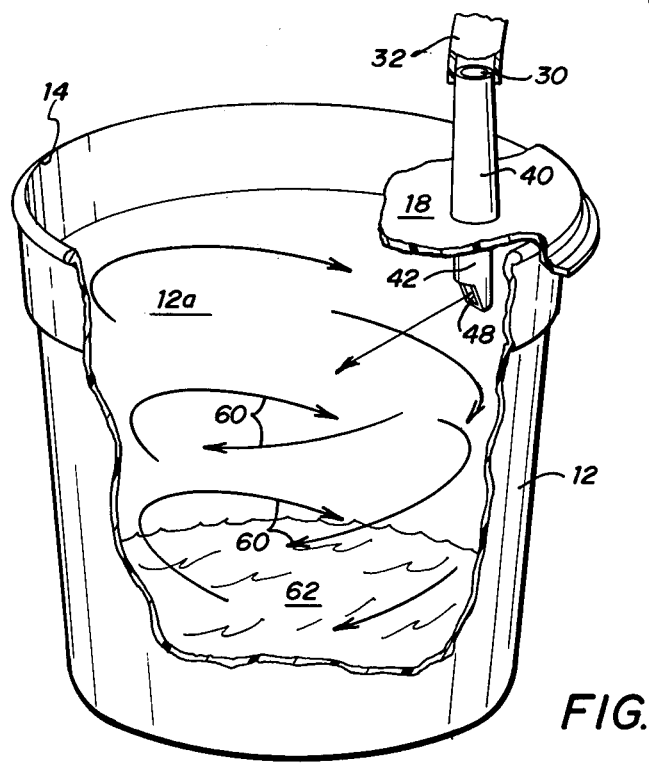
FIG. 3 is a perspective view of a suction canister utilizing the deflector of the present invention illustrating the helical flow path of inlet fluid within a suction canister.

FIG. 3 illustrates the operation of the present deflector 34. Fluid being drained from a patient during a surgical operation is transported through tube 32 to fluid inlet port 30 for entry into upper end 34a of deflector 34. The received fluid flows through bore 46 and exits deflector 34 through aperture 48 at lower end 34b of deflector 34. Due to the positioning of deflector 34 with respect to the interior sidewalls 12a of suction canister 12, the received fluid exits deflector 34 tangentially to interior walls 12a of suction canister 12. Direct and abrupt contact between the fluid and the canister sidewalls is thus prevented. Additionally, due to the incline of upper surface 54 of bottom wall 52, the received fluid is directed slightly downwardly towards bottom 12b of suction canister 12.

The resulting fluid flow from deflector 34 is generally indicated by the direction of arrows 60 which indicate a substantially helical path of the received fluid flowing around interior walls 12a of suction canister 12. The circumferential flow around the interior walls 12a of suction canister 12 functions to retard and reduce the high velocity impact of the received fluid against interior walls 12a and fluid 62 collected within suction canister 12. Because the energy of the received fluid is dissipated as the fluid flows to the bottom 12b of fluid canister 12, the fluid gently enters the fluid collected at the bottom of canister 12. The generation of aerosol droplets is effectively prevented. Additionally, since the received fluid does not directly impinge upon the interior walls 12a of suction canister 12 and fluid 62, deflector 34 minimizes splash, bounce and foaming of fluid received by suction canister assembly 10. The minimization of splash, bounce and foaming effectively prevents aerosol droplet generation and entry of fluid into vacuum shut-off valve 36 which would cause contamination and damage to the vacuum system. Since the received fluid does not enter below the level of fluid 62 collected in suction canister 12, swells and waves formed within canister 12 are effectively eliminated to prevent airborn particles and large droplets from drowning shut-off valve 36.

It can therefore be seen that the present deflector for use in a suction canister assembly for draining fluid from a patient directs received fluid to flow in a substantially helical path around the interior walls of the suction canister thereby retarding the flow of the received fluid within the suction canister to effectively prevent aerosol droplet generation and entry of fluid into the suction port. In addition, the deflector of the present invention minimizes splash, bounce and foaming of fluid received by a suction canister.

Whereas the present invention has been described with respect to specific embodiments thereof, it will be understood that various changes and modifications will be suggested to one skilled in the art and it is intended to encompass such changes and modifications as fall within the scope of the appended claims.

What is claimed is:

1. A suction system for receiving and retaining fluids drained from a source comprising:
   a canister with a vertical central axis having a closed bottom, substantially cylindrical sidewalls and an open top;
   a detachable circular cover adapted to selectively close said open top having an interior surface and an exterior surface and means for forming a vacuum-tight seal between said canister and said cover;
   said cover including a vacuum port for connection to a vacuum source to apply vacuum to the interior of said canister;
   said cover further including a deflector having an inlet port for admitting fluid into the interior of said canister and having an upper and lower end, said deflector being a tubular body having a vertical axis disposed in a parallel spaced-apart relationship with the canister central axis such that said deflector is positioned near the perimeter of said cover;
   said cover, vacuum port and deflector being one contiguous piece of material;
   said upper end of said deflector disposed above said exterior surface of said cover and slightly tapered from said exterior surface of said cover to receive an inlet tube;
   said lower end of said deflector disposed below the interior surface of said cover and being partially closed by a bottom wall extending across said lower end and ending at a bottom wall edge, said lower end having two sidewalls and a top wall forming with said bottom wall edge a rectangular aperture, said top wall being a horizontal surface, said bottom wall having an interior surface inclined slightly downward, said sidewalls being inclined with respect to said axis of said deflector such that the midpoint of said topwall is at a greater radial distance from said axis than the midpoint of said bottom wall edge; and
   said rectangular aperture positioned in said deflector such that a stream of fluid exiting said aperture impinges on said sidewalls of said canister at an incident angle sufficiently small to reduce the velocity impact of the stream of fluid and create a unidirectional circumferential helical flow of said stream of fluid around the sidewalls of said canister, wherein the velocity of the fluid exiting said deflector is sufficiently retarded to effectively prevent the formation of aerosal droplet formation and entry of admitted fluid into said vacuum port.

* * * * *